United States Patent
Lu

(10) Patent No.: US 11,268,139 B2
(45) Date of Patent: Mar. 8, 2022

(54) NUCLEIC ACID ISOTHERMAL SELF-AMPLIFICATION METHOD

(71) Applicant: Xinhua Lu, Shanghai (CN)

(72) Inventor: Xinhua Lu, Shanghai (CN)

(*) Notice: Subject to any disclaimer, the term of this patent is extended or adjusted under 35 U.S.C. 154(b) by 102 days.

(21) Appl. No.: 16/099,232

(22) PCT Filed: Jun. 7, 2017

(86) PCT No.: PCT/CN2017/087414
§ 371 (c)(1),
(2) Date: Nov. 6, 2018

(87) PCT Pub. No.: WO2017/215500
PCT Pub. Date: Dec. 21, 2017

(65) Prior Publication Data
US 2019/0211384 A1 Jul. 11, 2019

(30) Foreign Application Priority Data
Jun. 13, 2016 (CN) .......................... 201610420179.5

(51) Int. Cl.
| | | |
|---|---|---|
| *C12Q 1/68* | (2018.01) | |
| *C12Q 1/6851* | (2018.01) | |
| *C12N 9/12* | (2006.01) | |
| *C12N 15/86* | (2006.01) | |
| *C12Q 1/6869* | (2018.01) | |
| *C40B 40/08* | (2006.01) | |

(52) U.S. Cl.
CPC ......... *C12Q 1/6851* (2013.01); *C12N 9/1252* (2013.01); *C12N 15/86* (2013.01); *C12Q 1/68* (2013.01); *C12Q 1/6869* (2013.01); *C40B 40/08* (2013.01); *C12N 2310/20* (2017.05); *C12N 2310/531* (2013.01); *C12Q 2600/16* (2013.01)

(58) Field of Classification Search
CPC .............................. C12Q 1/6844; C12Q 1/68
See application file for complete search history.

(56) References Cited

U.S. PATENT DOCUMENTS

| | | | | |
|---|---|---|---|---|
| 7,368,265 B2 * | 5/2008 | Brenner | ................... | C12P 19/34 435/91.2 |
| 2012/0196279 A1 * | 8/2012 | Underwood | ............ | C12P 19/34 435/6.1 |

FOREIGN PATENT DOCUMENTS

| | | |
|---|---|---|
| CN | 101415838 A | 4/2009 |
| CN | 102084001 A | 6/2011 |
| CN | 103146684 A | 6/2013 |
| CN | 104164488 A | 11/2014 |
| CN | 104862400 A | 8/2015 |
| CN | 105442054 A | 3/2016 |
| JP | 2012529904 A | 11/2012 |
| WO | 2009120372 A2 | 10/2009 |
| WO | 2010146349 A1 | 12/2010 |
| WO | 2013096802 A1 | 6/2013 |
| WO | 2016022557 A1 | 2/2016 |
| WO | 2016028887 A1 | 2/2016 |
| WO | 2016059363 A1 | 4/2016 |

OTHER PUBLICATIONS

Mitas, Hairpin properties of single-stranded DNA containing a GC-rich triplet repeat (CTG)15, Nucleic Acids Research, 23(6): 1050-1059, 1995. (Year: 1995).*
Loop-mediated Isothermal Amplification (LAMP) of DNA.
Multiplex Loop-mediated Isothermal Amplification Detection by Sequence-Based Barcodes Coupled with Nicking Endonuclease-Mediated Pyrosequencing.
Amplified detection of nucleic acid by G-quadruplex based hybridization chain reaction.
Real-Time Detection of Isothermal Amplification Reactions with Thermostable Catalytic Hairpin Assembly.
The EESR dated Jan. 9, 2020 by the EPO.
The ISR dated Sep. 1, 2017 by WIPO.
A flexible and efficient template format for circular consensus sequencing and SNP detection.

* cited by examiner

*Primary Examiner* — Samuel C Woolwine
*Assistant Examiner* — Carolyn L Greene
(74) *Attorney, Agent, or Firm* — Bayramoglu Law Offices LLC

(57) ABSTRACT

Provided is a nucleic acid isothermal self-amplification method comprising, adding suitable palindrome complementary sequences at both ends of a target template to form a stem-loop structure spontaneously, and providing reagents and conditions as needed to perform self-amplification. The method does not require addition of additional amplification primers. The reagent comprises a DNA polymerase having a strand displacement activity. The method does not rely on exogenous amplification primers for amplification, has a constant amplification temperature without a complex temperature control equipment, and achieves rapid amplification. The amplification product is a long single-stranded DNA of a continuous complementary sequence and can be applied to special occasions. In addition, the amplification has no GC bias.

5 Claims, 5 Drawing Sheets

Specification includes a Sequence Listing.

SEQUENCE LISTING

```
<160> NUMBER OF SEQ ID NOS: 8

<210> SEQ ID NO 1
<211> LENGTH: 98
<212> TYPE: DNA
<213> ORGANISM: Artificial Sequence
<220> FEATURE:
<223> OTHER INFORMATION: Hind Standard 1

<400> SEQUENCE: 1
```

```
tatatatata tatatatata tatatatata agcttgcagg gtccgaggta acagagccaa    60
cctatttacg tgctgcaagc ttgcagcacg taaatagg                            98
```

<210> SEQ ID NO 2
<211> LENGTH: 59
<212> TYPE: DNA
<213> ORGANISM: Artificial Sequence
<220> FEATURE:
<223> OTHER INFORMATION: Hind Standard 2

<400> SEQUENCE: 2

```
gcagggtccg aggtaacaga gccaacctat ttacgtgctg caagcttcac gtaaatagg    59
```

<210> SEQ ID NO 3
<211> LENGTH: 22
<212> TYPE: DNA
<213> ORGANISM: Artificial Sequence
<220> FEATURE:
<223> OTHER INFORMATION: qPCR Pre-primer

<400> SEQUENCE: 3

```
cgcgcgtagc agcacgtaaa ta                                            22
```

<210> SEQ ID NO 4
<211> LENGTH: 16
<212> TYPE: DNA
<213> ORGANISM: Artificial Sequence
<220> FEATURE:
<223> OTHER INFORMATION: qPCR Back primer

<400> SEQUENCE: 4

```
gtgcagggtc cgaggt                                                   16
```

<210> SEQ ID NO 5
<211> LENGTH: 88
<212> TYPE: DNA
<213> ORGANISM: Artificial Sequence
<220> FEATURE:
<223> OTHER INFORMATION: Hind Standard 21

<400> SEQUENCE: 5

```
tatatatata tatatatata agcttgcagg gtccgaggta acagagccaa cctatttacg    60
tgctgcaagc ttgcagcacg taaatagg                                      88
```

<210> SEQ ID NO 6
<211> LENGTH: 82
<212> TYPE: DNA
<213> ORGANISM: Artificial Sequence
<220> FEATURE:
<223> OTHER INFORMATION: Hind Standard 15

<400> SEQUENCE: 6

```
tatatatata taagcttg cagggtccga ggtaacagag ccaacctatt tacgtgctgc      60
aagcttgcag cacgtaaata gg                                            82
```

<210> SEQ ID NO 7
<211> LENGTH: 76
<212> TYPE: DNA
<213> ORGANISM: Artificial Sequence
<220> FEATURE:
<223> OTHER INFORMATION: Hind Standard 9

<400> SEQUENCE: 7

```
tatatataag cttgcagggt ccgaggtaac agagccaacc tatttacgtg ctgcaagctt            60
gcagcacgta aatagg                                                           76

<210> SEQ ID NO 8
<211> LENGTH: 69
<212> TYPE: DNA
<213> ORGANISM: Artificial Sequence
<220> FEATURE:
<223> OTHER INFORMATION: Hind Standard 0

<400> SEQUENCE: 8
aagcttgcag ggtccgaggt aacagagcca acctatttac gtgctgcaag cttgcagcac            60
gtaaatagg                                                                   69
```

NUCLEIC ACID ISOTHERMAL SELF-AMPLIFICATION METHOD

CROSS REFERENCE TO THE RELATED APPLICATIONS

This application is the national phase entry of International Application No. PCT/CN2017/087414, filed on Jun. 7, 2017, which is based upon and claims priority to Chinese Patent Application No. 201610420179.5, filed on Jun. 13, 2016, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBSKSZ003-POA_SequenceListing.txt, created on 07/22/2021 and is 2,217 bytes in size.

TECHNICAL FIELD

The application relates to an isothermal self-amplification method of a nucleic acid, and it is in the technical field of nucleic acid amplification.

BACKGROUND

In the past decades, the nucleic acid amplification technology has made a revolutionary contribution to molecular biological researches and the pathogenic microorganism detections. The isothermal amplification is an in vitro amplification process of a nucleic acid, and the whole reaction is maintained at a constant temperature. Using such process, rapid nucleic acid amplification is achieved by adding an enzyme with different activity and an individually specific primer. Loop-mediated isothermal amplification (LAMP), rolling circle amplification (RCA), single-primer isothermal amplification (SPIA), helicase-dependent isothermal amplification (HAD), strand-displacement amplification (SDA) and the like, are common isothermal amplification methods. In the presence of primers, these methods are liable to generate non-specific amplifications due to the DNA polymerase with chain replacement activity.

The isothermal amplification is widely used in the second-generation nucleic acid sequencing, and it also plays an important role in the third-generation nucleic acid sequencing. For example, in the sequencing technology of Pacific Biosciences (U.S. Pat. No. 9,404,146), RCA was used for repeated sequencing of one segment, and the accuracy of sequencing results was greatly improved through software calibration. Similarly, in the sequencing technology of Oxford Nanopore, if the similar technology was used, the accuracy of sequencing results can also be greatly improved (INC-Seq: Accurate single molecule reads using nanopore sequencing, Li et al. science (2016) 5). However, as the sequencing principle of Oxford Nanopore is so special that the use of RCA leads that the process was complicated, the amplification was not heterogeneous enough, and the sequencing result was influenced.

SUMMARY OF THE INVENTION

The invention aims to solve the problems mentioned above. Herein provided is an isothermal self-amplification method of a nucleic acid. The purpose of the invention is realized by the following technical solutions.

An isothermal self-amplification method of a nucleic acid comprising the following steps:
  a) adding a DNA linker of a desired sequence at both ends of a target template;
  c) providing a reagent and a condition required by the reaction;
the DNA linker of the desired sequence is a linear nucleic acid fragment which itself spontaneously forms a stem-loop structure, and no additional primer is added in the self-amplification method; and
the reagent comprises a DNA polymerase with chain replacement activity or any other enzyme with chain replacement activity.

Preferably, the DNA polymerase is Bst enzyme or any other DNA polymerase.

Preferably, the DNA linker added at both ends of the target template is a linear nucleic acid fragment having a palindromic complementary sequence, which itself spontaneously forms a stem-loop structure to trigger the extension amplification by the DNA polymerase.

Preferably, the sequence of the DNA linker may be, but not limited to, a repeating sequence of base combination AT, or a repeating sequence of combination AATT, or a repeating sequence of combination GC. The DNA linker may have modified bases. The modification may be phosphorothioate modification or the like.

Preferably, the product of the amplification method is a folding-complementary, single-stranded DNA and it has a tandem repeating sequence.

Use of a nucleic acid isothermal self-amplification method, wherein the method can be used for establishing a two-generation sequencing library, and in the library establishing method, cyclic amplification is carried out by breaking a genomic DNA long chain into small fragments and adding a linker comprising a desired sequence to both ends of the fragments; or a selective amplification is carried out by selectively inserting a linker fragment through a transposon, a CRISPR/cas9 system and the like, and the amplification product is a tandem repeating sequence.

Using certain sequencing instruments such as a nanopore sequencing instrument, the sequencing library prepared by such method can increase the sequencing frequency of the target sequence so as to improve the sequencing accuracy.

The main advantages are:
  1) the target fragment can be rapidly and effectively amplified under isothermal condition;
  2) the amplification can be carried out without primers after an appropriate palindromic complementary sequence is added at an end of DNA;
  3) the amplification product is a long, single-stranded DNA of a continuous complementary sequence and can be applied to special occasions; and
  4) the amplification has no GC bias.

BRIEF DESCRIPTION OF DRAWINGS

The embodiments of the invention are described below with reference to the drawings.

DETAILED DESCRIPTION OF THE EMBODIMENTS

Figure 1:
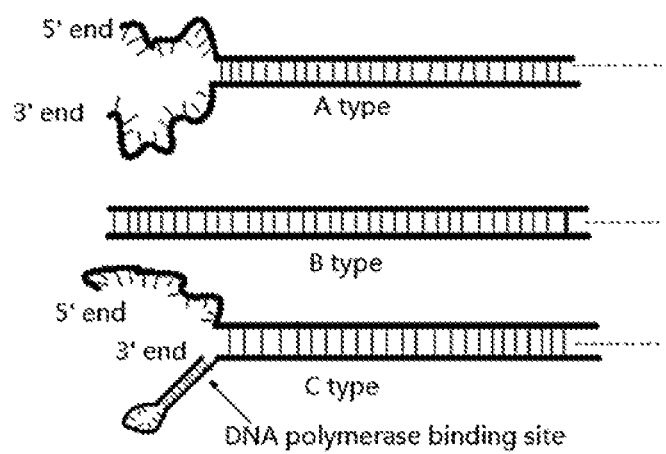
FIG. 1 is a schematic diagram of respiratory mechanism and conformation conversion of double-stranded DNA at its end.

Herein provided is an isothermal self-amplification method of a nucleic acid, wherein the product of the amplification method is a folding-complementary, single-stranded DNA, and said method comprises the following steps:
   a) adding a DNA linker of a desired sequence at both ends of a target template;
   c) providing a reagent and a condition required by the reaction;
the DNA linker of the desired sequence is a linear nucleic acid fragment which itself spontaneously forms a stem-loop structure, and no additional primer is added in the self-amplification method; the DNA linker is a linear nucleic acid fragment having a palindromic complementary sequence, which itself spontaneously forms a stem-loop structure to trigger the extension amplification by the DNA polymerase.

Using PCR, ligase, in-vitro transposon system and the like, an appropriate palindromic complementary sequence is added at a DNA linear end so as to form a stem-loop structure itself. The self-amplification method needs no additional primers, and the product of the amplification method is a folding-complementary, single-stranded DNA.

The reagent comprises a DNA polymerase with chain replacement activity or any other DNA polymerase.

The DNA polymerase is Bst enzyme. The Bst enzyme has no GC bias so that the amplification product has an improved homogeneity.

Herein provided is use of a nucleic acid isothermal self-amplification method, wherein the method can be used for establishing a two-generation sequencing library. Said method comprises the following steps: fragmentation is carried out for DNA, and the DNA fragments are subject to a ligase reaction during which a sequence suitable for self-amplification is added at both ends; or fragments are selectively added using a transposon, CRISPR/cas9 system and the like, so that a sequence suitable for self-amplification is added to an end of the DNA fragments for isothermal self-amplification.

The principle of the present self-amplification is described in detail below.

According to DNA respiration mechanism, the end of double-stranded DNA is in the dynamic balance as it is melted into a free single-stranded form and annealed into a complementary double-stranded form. The higher the temperature is, the stronger the respiration is and the more significant the melting at the end is. During this procedure, a foreign pairing primer may intrude and bind to one strand of DNA to extend in the presence of DNA polymerase with strand replacement activity (isothermal amplification method for next-generation sequencing: 14320-14323, PNAS, Aug. 27, 2013, vol. 110, no. 35).

First, using PCR, a linker connection, directed recombination of DNA and the like, a special DNA sequence is introduced at an end of a target gene. Said DNA sequence is a palindromic sequence, which may form a stem-loop structure by self-pairing and then amplify itself using the DNA respiration phenomenon. Said amplification needs no additional foreign primers, and occurs at 3' end in the presence of DNA polymerase with chain replacement activity using itself as a template. After the first cycle of amplification is completed, the newly formed 3' end is complementary to the original 5' end, and it may form a palindromic structure using such self complementary pairing. A new cycle of amplification then occurs, where newly formed 3' end is complementary to the old 5' end for further cycles of amplification. Each single strand of the DNA double-stranded sequence occurs similar reaction at the same time, and the final product is two multi-repeating, complementary DNA single strands.

Complementary bases in double-stranded DNA are connected each other through hydrogen bond. Because adenine (A) and thymine (T) have two hydrogen bonds, and guanine (G) and cytosine (C) have three hydrogen bonds, the AT pairing is easier to break compared with the GC pairing. For the DNA respiration phenomenon, in order to form a hairpin structure conformation at the 3' end, it requires that there are less pairing bases at the end and that the loop portion cannot bind via pairing due to spatial structure, in comparison with a complete-complementary conformation of DNA. Therefore, in order to increase the probability of successfully forming a hairpin structure at the 3' end, the content of the AT at the end can be increased, the length of the free single-strand can be increased, and a short repeating sequence can be used, such as TA, TAA, TTAA and other repeating sequences, so that pairing is easier to occur.

In the isothermal self-amplification process, once an appropriate sequence is added at the end of a target fragment, the self-amplification can still occur even after the primer is removed. During the amplification process, as the amplification products are continuous complementary sequences, it can be quickly paired to form a double-stranded structure due to the spatial short-distance effect, almost no single-stranded DNA is exposed, and non-specific amplification is substantially eliminated. In high-throughput sequencing, such as single cell sequencing, isothermal self-amplification can not only eliminate the GC bias, but also obtain a better homogeneity in comparison with PCR method.

Figure 5:
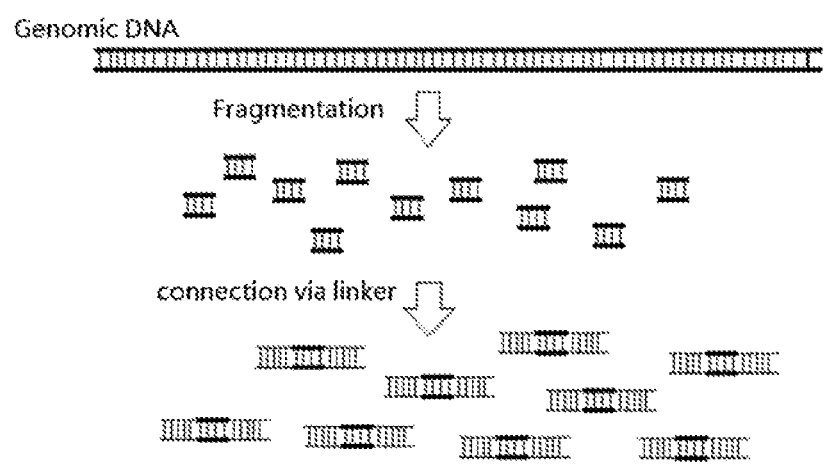
FIG. 5 is a schematic diagram of change in sequence structure during the construction of a two-generation sequencing library.

The final product of the isothermal self-amplification is single-stranded DNA of a continuous complementary sequence. In one aspect, it can be cut into short segments by means such as enzyme digestion, and in another aspect, such long repeating sequence can be applied to special occasions such as sequencing. As shown in FIG. 5, a two-generation sequencing library is constructed. The genomic DNA is long in sequence, and it may be subject to mechanical shearing (such as magnetic-bead shaking) or enzyme digestion to break into small fragments at the length of about several hundred bases, followed by the addition at an end of a linker comprising sequence suitable for self-amplification using ligase and isothermal self-amplification. During the amplification process, no primers are used, and no complete melting of the duplex occurs. Therefore, compared with PCR method, the product has better homogeneity and no GC bias.

In combination with the accompanied drawings, the following describes use of different methods to produce a stem-loop structure suitable for self-amplification reaction.

Respiratory mechanism and conformation conversion at the ends of double-stranded DNA are shown in FIG. 1. The linear, completely complementary, double-stranded DNA (B type), and under physiological condition the free state at ends where double strands are opened (A type), are two states in a dynamic balance and can be converted each other. Under a high temperature or other conditions, the respiration is strong, and when the end sequence is self-complementary, a stem-loop structure (C type) may be generated, and a binding site for the DNA polymerase is generated so that the amplification reaction is triggered.

Figure 2:
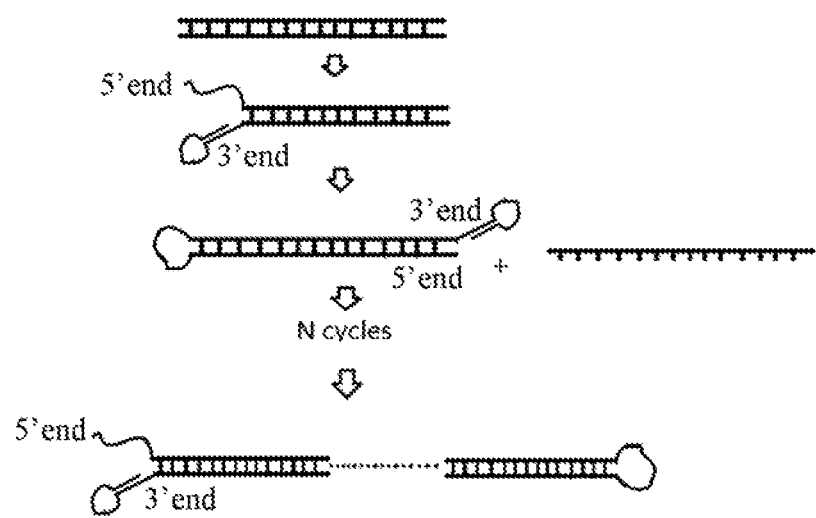
FIG. 2 is a schematic diagram of self-amplification process of DNA having sequences at both ends (3'end and 5'end) suitable for the self-amplification.
Figure 3:
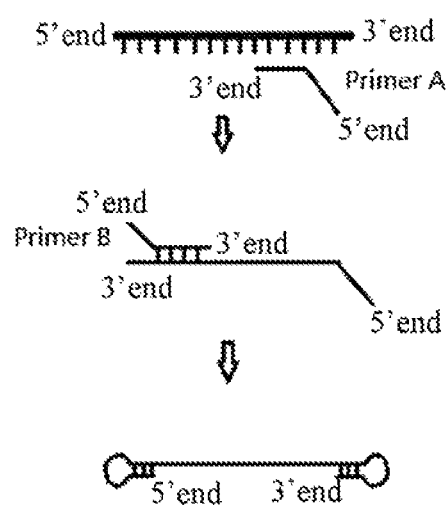
FIG. 3 is a schematic diagram of a process for adding an appropriate sequence at an end of a target gene.

FIG. 2 shows a self-amplification procedure of a double-stranded DNA sequence comprising sequences suitable for the self-amplification at both ends (3' and 5' ends). Firstly, a double-stranded, linear DNA sequence is showed; secondly, a hairpin structure is present at 3' end and a DNA polymerase with chain replacement activity is bound thereto to carry out chain replacement reaction; thirdly, the self-amplification is completed, the antisense strand is replaced (the antisense strand is also subject to a synchronous reaction), the copy number is doubled, and the new 3' end is generated using 5' end as a template so that a hairpin structure can still be generated; fourthly, n cycles of amplification occurs; and fifthly, the product obtained after the amplification cycles is a long, single-stranded DNA, wherein the copy number is 2 to the power of n. FIG. 3 shows a process of adding an appropriate sequence at an end of a target gene by PCR method. Firstly, the 3' end of the primer A is a sequence complementary to the target gene, the 5' end is an added sequence, the primer is bound after a high-temperature chain melting, and an antisense strand is formed by PCR amplification; secondly, the 3' end of the primer B is a sequence complementary to the target gene, the 5' end is an added sequence, and the primer is bound after a high-temperature chain melting to carry out PCR amplification; thirdly, the amplification product forms a loop itself after a high-temperature melting, serving as a starting substance for isothermal self-amplification.

Figure 4:
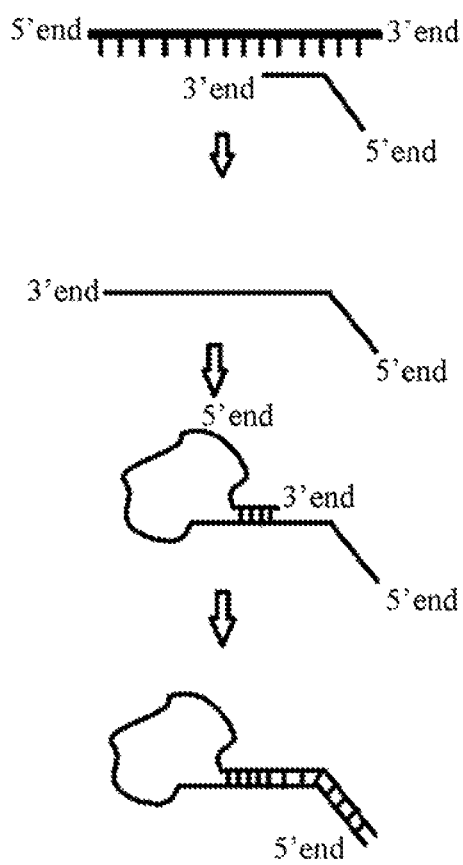
FIG. 4 is a schematic diagram of a process for adding an appropriate sequence at an end of a target gene via a non-specific amplification method.

FIG. 4 shows a process for adding an appropriate sequence at an end of a target gene by a non-specific amplification method. Firstly, primer A is bound after high-temperature melting; secondly, antisense strand is formed by DNA polymerase amplification; thirdly, some DNA polymerases with strand replacement activity, e.g., Bst, can bind and perform the amplification even the primer and the template are not completely matched, which is generally unfavorable to the reaction, and if DNA is long enough, by using this property, 3' end may fold and nonspecifically bind to itself to proceed amplification to obtain a complementary sequence at 5' end; fourthly, it serves as a starting substance for isothermal self-amplification.

Amplification Efficiency Detection

In order to eliminate interferences from such as excess primers, template nucleic acids and the like so as to better determine the efficiency of DNA isothermal self-amplification, a single-stranded DNA sequence comprising an isothermal self-amplification sequence at an end, was synthesized. It is named as Hind standard substance 1, and is set forth by SEQ ID NO: 1 (all the DNA sequences below are synthesized by Songon Biotech (Shanghai) Co. Ltd.).

TATATATATATATATATATATATATATATAAGCTTGCAGGGTCCGAGGT
AACAGAGCCAACCTATTTACGTGCTGCAAGCTTGCAGCACGTAAATAGG

A Single-stranded DNA sequence without the isothermal self-amplification sequence at the end was also synthesized (the complementary sequence at the end is removed). It is named as Hind standard substance 2, and is set forth by SEQ ID NO: 2.

GCAGGGTCCGAGGTAACAGAGCCAACCTATTTACGTGCTGCAAGCTTCAC
GTAAATAGG

A constant-temperature amplification reaction system of 25 µl was provided, wherein each dNTP is 0.2 mM H$_2$O, Bst DNA Polymerase Buffer 1×, 4 mM MgSO4, warm strat Bst Polymerase 8U (purchased from NEB corporation), Hind standard substance is about 100 µM. The reaction was carried out for 1 hour at 60° C.

The reaction product was subject to enzyme digestion by Hind III (purchased from NEB Company) and qPCR detection.

qPCR forward primer:
(SEQ ID NO: 3)
CGCGCGTAGCAGCACGTAAATA qPCR reverse primer:
(SEQ ID NO: 4)
GTGCAGGGTCCGAGGT A qPCR reaction system of 20 µl was provided, comprising primers at a final concentration of 200 nM, Fast sybgreen Mix 1×, and an enzyme-digestion product of 3 µl. The reaction procedure comprises 95° C. for 30 seconds, and 45 cycles of 60° C. for 20 seconds and 95° C. for 5 seconds.

The detection data are shown in table 1.

TABLE 1

| | Ct value | | |
|---|---|---|---|
| | Direct qPCR | qPCR after isothermal amplification enzyme digestion | delt Ct value |
| Hind standard substance 1 | 21 | 12 | −9 |
| Hind standard substance 2 | 20 | 23 | 3 |

The result shows that the Hind standard substance 1 was amplified by about 1000 times, and the Hind standard substance 2 almost had no amplification, indicating a nucleic acid fragment having a specific structure can be subject to a constant-temperature self-amplification.

Detecting Relationship Between Amplification Efficiency and Initial Concentration In order to eliminate interferences from such as excess primers, template nucleic acids and the like so as to better determine the DNA isothermal self-amplification efficiency, Hind standard substance 1 was synthesized, and different initial concentrations were used.

The isothermal amplification and qPCR were carried out as described in example 1, and the reaction was performed at 60° C. for 2 hours.

Data are shown in table 2

TABLE 2

| | | Ct values | | |
|---|---|---|---|---|
| | Initial concentration of Hind standard substance 1 | Direct qPCR | qPCR after isothermal amplification enzyme digestion | delt Ct value |
| 1 | 500 pM | 19 | 7 | −12 |
| 2 | 50 pM | 23 | 9 | −14 |

TABLE 2-continued

| | Ct values | | | |
|---|---|---|---|---|
| | Initial concentration of Hind standard substance 1 | Direct qPCR | qPCR after isothermal amplification enzyme digestion | delt Ct value |
| 3 | 5 pM | 26 | 12 | −14 |
| 4 | 500 fM | 29 | 16 | −13 |
| 5 | 50 fM | 31 | 19 | −12 |
| 6 | 5 fM | 31 | 24 | −7 |
| 7 | 0.5 fM | 31 | 27 | −4 |
| 8 | 0.05 fM | 31 | 30 | −1 |
| 9 | 0.005 fM | 31 | 31 | 0 |
| 10 | 0 | 31 | 31 | 0 |

Results show that the amplification can be carried out even if there is near one copy of a nucleic acid segment in the solution, and the amplification factor was about 1000, indicating that the isothermal amplification occurs spontaneously and it needs no primers.

Relationship Between Amplification Efficiency and Terminal Sequence

In order to eliminate interferences from such as excess primers, template nucleic acids and the like so as to better determine the DNA isothermal self-amplification, fragments were synthesized and terminal sequences at different lengths were used.

```
Hind standard substance 1:
                                          (SEQ ID NO: 1)
TATATATATATATATATATATATATATATATAAGCTTGCAGGGTCCGAGGTA
ACAGAGCCAACCTATTTACGTGCTGCAAGCTTGCAGCACGTAAATAGG Hind standard substance 21:
                                          (SEQ ID NO: 5)
TATATATATATATATATATAAGCTTGCAGGGTCCGAGGTAACAGAGCCAA
CCTATTTACGTGCTGCAAGCTTGCAGCACGTAAATAGG Hind standard substance 15:
                                          (SEQ ID NO: 6)
TATATATATATATAAGCTTGCAGGGTCCGAGGTAACAGAGCCAACCTATT
TACGTGCTGCAAGCTTGCAGCACGTAAATAGG Hind standard product 9:
                                          (SEQ ID NO: 7)
TATATATAAGCTTGCAGGGTCCGAGGTAACAGAGCCAACCTATTTACGTG
CTGCAAGCTTGCAGCACGTAAATAGG Hind standard substance 0:
                                          (SEQ ID NO: 8)
AAGCTTGCAGGGTCCGAGGTAACAGAGCCAACCTATTTACGTGCTGCAAG
CTTGCAGCACGTAAATAGG
```

The isothermal amplification and qPCR were performed as described in example 1, and the reactions were carried out at 60° C. for 2 hours.

Data are shown in table 3.

TABLE 3

| | | Ct values | | |
|---|---|---|---|---|
| | | Direct qPCR | qPCR after isothermal amplification enzyme digestion | delt Ct value |
| 1 | Hind standard substance 1 | 27 | 13 | −14 |
| 2 | Hind standard substance 21 | 27 | 15 | −12 |
| 3 | Hind standard substance 15 | 29 | 15 | −14 |
| 4 | Hind standard substance 9 | 29 | 22 | −7 |
| 5 | Hind standard substance 0 | 27 | 24 | −3 |

The results show that the amplification efficiency was about 1000 times when the terminal repeating TA sequence was at the length of 30, 21 or 15, and the amplification efficiency was about 100 times when the terminal repeating TA sequence was at the length of 9, and the amplification was hardly caused when the length was 0, indicating that the isothermal self-amplification is dependent on the terminal TA repeating sequence.

Relationship Between Amplification Factor and Time

In order to eliminate interferences from such as excess primers, template nucleic acids and the like so as to better determine the DNA isothermal self-amplification efficiency, a single-stranded DNA sequence having an isothermal self-amplification sequence, Hind standard substance 1, was synthesized.

The isothermal amplification and qPCR were carried out as described in example 1. Different time for the reaction times at 60° C. were used.

Data are shown in table 4.

TABLE 4

| | time (minutes) | Ct values (qPCR after isothermal amplification enzyme digestion) |
|---|---|---|
| 1 | 0 | 28 |
| 2 | 1 | 26 |
| 3 | 5 | 23 |
| 4 | 20 | 20 |
| 5 | 60 | 17 |

The results indicate that the longer the isothermal self-amplification time is, the higher the amplification factor is; and the amplification efficiency is slightly higher at the initiation stage. The invention further provides a plurality of specific embodiments, and all technical solutions formed by equivalent replacement or equivalent transformation fall within the scope of the invention.

What is claimed is:

1. A nucleic acid isothermal self-amplification method, comprising the following steps:
   a) adding a DNA linker of a desired sequence to both 3' and 5' ends of a target linear DNA template; and
   b) providing a reagent and a temperature required by an isothermal self-amplification of the target linear DNA template;
   wherein the DNA linker of the desired sequence is a linear nucleic acid fragment spontaneously forming a stem-loop structure within the DNA linker to trigger the isothermal self-amplification of the target linear DNA template, in the presence of a DNA polymerase, to generate a folding-complementary, single-stranded DNA having a tandem of repeated sequences, and no additional primer is added in the isothermal self-amplification;
   wherein the DNA linker added at both ends of the target linear DNA template is a linear nucleic acid fragment having a palindromic complementary sequence spontaneously forming the stem-loop structure to trigger the isothermal self-amplification of the target linear DNA template in the presence of the DNA polymerase;
   the sequence of the DNA linker is a repeating sequence of base combination AT, or a repeating sequence of base combination AATT, or a repeating sequence of combination GC, and wherein the DNA linker has modified bases; and
   wherein the reagent comprises the DNA polymerase.

2. The nucleic acid isothermal self-amplification method according to claim 1, wherein the DNA polymerase is Bst enzyme.

3. A method for establishing a sequencing library, comprising the following steps:
   a) breaking a genomic DNA long chain into small fragments, thereby creating at least two target linear DNA templates; and
   b) performing the nucleic acid isothermal self-amplification method according to claim 1 on each of the at least two target linear DNA templates.

4. The method according to claim 3, wherein the DNA linker is added through a transposon or a CRISPR/Cas9 system.

5. The method according to claim 3, wherein the DNA polymerase is Bst enzyme.

* * * * *